(12) United States Patent
Schindler, III

(10) Patent No.: US 10,281,367 B1
(45) Date of Patent: *May 7, 2019

(54) SYSTEM AND METHOD FOR MANAGING SAMPLE COLLECTION DATA AND DOCUMENTATION

(71) Applicant: SampleServe, Inc., Traverse City, MI (US)

(72) Inventor: Albert Russell Schindler, III, Traverse City, MI (US)

(73) Assignee: SampleServe, Inc., Traverse City, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,269

(22) Filed: Dec. 18, 2018

Related U.S. Application Data

(63) Continuation-in-part of application No. 15/635,416, filed on Jun. 28, 2017, now Pat. No. 10,198,676.

(51) Int. Cl.
  *G01N 1/02* (2006.01)
  *G06K 19/06* (2006.01)

(52) U.S. Cl.
  CPC ......... *G01N 1/02* (2013.01); *G06K 19/06037* (2013.01)

(58) Field of Classification Search
  CPC .. G06K 17/0022; G06K 1/121; G06K 7/1413; G06K 2007/10524; B41J 3/4075
  USPC .............................................. 235/385, 462.01
  See application file for complete search history.

(56) References Cited

U.S. PATENT DOCUMENTS

| | | | | | |
|---|---|---|---|---|---|
| 5,164,575 | A * | 11/1992 | Neeley | ............. | A61B 5/117 235/472.01 |
| 5,166,498 | A * | 11/1992 | Neeley | ............. | A61B 5/117 235/375 |
| 5,401,110 | A * | 3/1995 | Neeley | ............. | B01L 3/5453 235/375 |
| 7,278,579 | B2 * | 10/2007 | Loffredo | ............. | G06F 3/1205 235/375 |
| 2004/0219074 | A1 * | 11/2004 | Childers | ............. | B01L 3/5085 422/534 |
| 2006/0180659 | A1 * | 8/2006 | Loffredo | ............. | G06F 3/1205 235/380 |
| 2009/0048870 | A1 * | 2/2009 | Godshall | ............. | G16H 10/40 705/3 |

\* cited by examiner

*Primary Examiner* — Paultep Savusdiphol
(74) *Attorney, Agent, or Firm* — Marshall & Melhorn, LLC

(57) ABSTRACT

A system and methods for more quickly, accurately, and efficiently collecting, tracking, and transmitting sample collection data and information. Specifically, this involves the generation of printed labels in the field comprising labels with unique identifiers corresponding to specific sample collection data and information. The labels are printed at the location of the sampling and are applied on the outside of sample collection devices and at the location of sample collection. Each unique identifier is associated with a unique record number in the Electronic Chain of Custody (ECOC), corresponding to a specific sample.

5 Claims, 9 Drawing Sheets

FIG. 8A

Low Flow Sampling Display

Site Name: Gas Station #5678

Sample Location/Well ID: MW-80

Operator Name: John Smith

[Picture] [Capture GPS]

Time to Next Data point: 1:32

[Stop data collection and start collecting sample & Print Labels]

[Re-Print Individual Sample Bottle Label.]

| pH | ORP (mV) | Conductivity (us/cm) | DO (mg/l) | Temp. (C) | Turbidity (NTU) |
|---|---|---|---|---|---|
| 8.75 | -63.8 | 1611.6 | 2.65 | 14.91 | 17.7 |

| Reading# | Time | Interval Time (sec) | DTW | Flow Rate (cc) | Running Vol (cc's) | pH | ORP (mV) | Conductivity (us/cm) | DO (mg/l) | Temp. (C) | Turbidity (NTU) |
|---|---|---|---|---|---|---|---|---|---|---|---|
| | | | | | | +/-0.1 | +/-10 | +/-3% | +/-0.3 | +/-3% | +/-10 |
| 1 | 10:00:00 | 180.0 | 20.70 | 300 | 1000 | 8.75 | -63.8 | 1611.6 | 2.65 | 14.91 | 17.7 |
| 2 | 10:03:00 | 180.0 | 20.89 | 300 | 2000 | 8.82 | -38.3 | 1585.2 | 2.31 | 15.06 | 56.3 |
| 3 | 10:06:30 | 210.0 | 20.95 | 200 | 3000 | 8.8 | -32 | 1619.2 | 1.8 | 13.86 | 42.4 |
| 4 | 10:10:00 | 210.0 | 20.96 | 200 | 4000 | 8.78 | -49.2 | 1617.2 | 1.49 | 14.38 | 12.1 |
| 5 | 10:13:30 | 210.0 | 20.96 | 200 | 5000 | 8.8 | -31 | 1601.0 | 1.31 | 14.47 | 11.2 |
| 6 | 10:17:00 | 210.0 | 20.97 | 200 | 6000 | 8.82 | -24.7 | 1609.9 | 1.15 | 14.61 | 7.42 |
| 7 | 10:20:30 | 210.0 | 20.97 | 200 | 7000 | 8.83 | -22.9 | 1616.1 | 1.08 | 15.23 | 5.79 |
| | | (calculated) | | | (calculated) | | | | | | |

FIG. 8B

Summary of Data

| Well ID | Sample Time | Elapsed Time (sec) | Total Drawdown (ft) | Ending Flow Rate(cc) | Total Vol Purged (L) | pH | ORP (mV) | Conductivity (us/cm) | DO (mg/l) | Temp. (C) | Turbidity (NTU) |
|---|---|---|---|---|---|---|---|---|---|---|---|
| MW-80 | 10:20:30 | 20:30 | 0.38 | 200 | 7.0 | 8.83 | -22.9 | 1616.1 | 1.08 | 15.23 | 5.79 |

Comments:

Push when done filling sample bottles.

Time Done Sampling   Flow Rate While Sampling(cc)
10:26:30                        100

Store data Upload & E-mail as one upon Sync!

Push to go to next location at this site

E-mail data now.

Upload data to web site now.

Grab Sampling

Site Name: Gas Station #5678

Sample Location/Well ID: Creek Location #1    Operator Name: John Smith

Picture
Capture GPS

Comments: Water is muddy from runoff

| Well ID | Sample Time | pH | ORP (mV) | Conductivity (us/cm) | DO (mg/l) | Temp. (C) | Turbidity (NTU) |
|---|---|---|---|---|---|---|---|
| Creek Location #1 | 10:20:30 | 8.75 | -63.8 | 1611.6 | 2.65 | 14.91 | 17.7 |

Store data Upload & E-mail as one upon Sync!

Print All Bottle Labels

E-mail data now.

Print individual Label

Upload data to web site now.

Push to go to next location at this site

FIG. 9

SYSTEM AND METHOD FOR MANAGING SAMPLE COLLECTION DATA AND DOCUMENTATION

PRIORITY CLAIM

This patent application claims priority to and the benefit of the filing date of the non-provisional patent application having application Ser. No. 15/635,416, filed on Jun. 28, 2017, which is incorporated herein in its entirety.

FIELD

This patent application relates generally to the management of sample collection data and documentation.

BACKGROUND

Sample testing facilities, such as laboratories, spend a considerable amount of time and money ordering, storing, recording, and requesting data and documentation pertaining to sample collection and tracking the custody and control of the samples. Chain of custody records are commonly utilized in these types of facilities due to the nature of the samples and the specific instructions and requirements for the collection and handling of the samples. As such, it is very important that no mistakes are made in collecting, tracking, recording, and transmitting the samples, such as mislabeling a sample with the incorrect sample identification or site project information. Thus, environmental facilities incur great expense and time to ensure that the custody and control of samples is well-documented and correct.

Currently, most laboratories receive sample data and documentation, such as handwritten notes, handwritten bottle labels, handwritten custody seals (such as stickers) on the outside of coolers, and handwritten lab instructions from field technicians that are collecting the samples. The laboratories then manually enter the data that they received from the field technicians into their systems, and sometimes add barcodes to the bottles and coolers. In addition, the laboratories manually note that relevant information on chain of custody (COC) forms into their data system and compare COC information to sample bottle information and/or sample cooler information. Along with the inefficiencies associated with such a process, laboratories often have trouble deciphering handwritten data and information, which results in inaccurate and/or lost information corresponding to a specific collected sample.

Chain of custody forms are necessary to document and track a sample collection process in order to know who possessed the sample and where the sample has been from the time of collection through delivery to a laboratory. The most important item in the chain of custody form is a unique identifier/label to identify the sample in each bottle, cooler, and/or container. A laboratory cannot complete a sample collection and analysis until it has a unique identifier on the bottle, container, and/or cooler corresponding to the sample. Laboratories commonly generate and add their own unique identifier to the bottle, container, and/or cooler in the form of a barcode or unique sample identification number. They then must manually record and match up all of the data and documentation received through a paper chain of custody form for a sample with the unique barcode or unique sample identification number. This process results in data entry errors and is unnecessarily time consuming and costly.

A further problem of having paper chain of custody forms is the inefficiency involved in marrying the actual sample bottles, containers, and coolers from the field with the data and documentation found in and associated with chain of custody forms. Turnaround time is often much slower with the current process since laboratories must wait to receive mailed copies of the chain of custody forms. The laboratory employees must then search for, process, and marry the chain of custody forms with the corresponding sample bottles. Thus, there is a need for a less time-consuming, more accurate, and more efficient system and method for managing the collection of sample data and documentation.

SUMMARY

What is provided is a system and methods for more accurately, securely, and efficiently collecting, tracking, and transmitting sample collection data and documentation. By eliminating the need to manually enter sample collection information, such as labels and chain of custody forms, many inaccuracies and confusions may be avoided. Also, project efficiencies are increased when sample collection data and documentation are immediately available as several costly and time-consuming steps may be eliminated.

In an embodiment, the method for managing collection data and/or information corresponding to at least one environmental sample using a mobile software application configured to operate on a mobile computing device comprises providing at least one first sample collection device; accessing the mobile software application on the mobile computing device; receiving a set of pre-configured instructions from the mobile software application for processing and analyzing field data at a site, wherein the field data comprises a plurality of parameters; and processing and analyzing the field data via the mobile computing device at the site. The method also comprises transmitting a signal to the mobile computing device based on the values of the plurality of parameters in the processed and analyzed field data, wherein the signal comprises instructions for when to collect the environmental sample, where to collect the environmental sample within the site, and the type of the environmental sample to collect; collecting the environmental sample at the site; printing a first label at the site corresponding to the first sample collection device and a second label at the site corresponding to a location of sample collection, wherein the first label includes a first unique identifier and the second label includes a second unique identifier, wherein the first unique identifier and the second unique identifier are both associated with the environmental sample; affixing the first label to the first sample collection device and placing the second label at the location of sample collection; transmitting an electronic chain of custody corresponding to the environmental sample to a computing system located remote from the site prior to delivering the first sample collection device to the computing system; and scanning the first unique identifier on the first sample collection device using a barcode reader in communication with the computing system to populate the collection data and/or information corresponding to the environmental sample and the electronic chain of custody in the computing system.

BRIEF DESCRIPTION OF THE DRAWINGS

The above, as well as other advantages of the present disclosure, will become readily apparent to those skilled in the art from the following detailed description when considered in light of the accompanying drawings in which:

FIG. 8a is a schematic plan view of an exemplary user interface for Low Flow Sampling Display of sample collection information and data generated using the system of FIG. 1;

FIG. 8b is a schematic plan view of an additional exemplary user interface for Low Flow Sampling Display of sample collection information and data generated using the system of FIG. 1; and FIG. 9 is a schematic plan view of an exemplary user interface for Grab Sampling of sample collection information and data generated using the system of FIG. 1.

DETAILED DESCRIPTION

Figure 1:
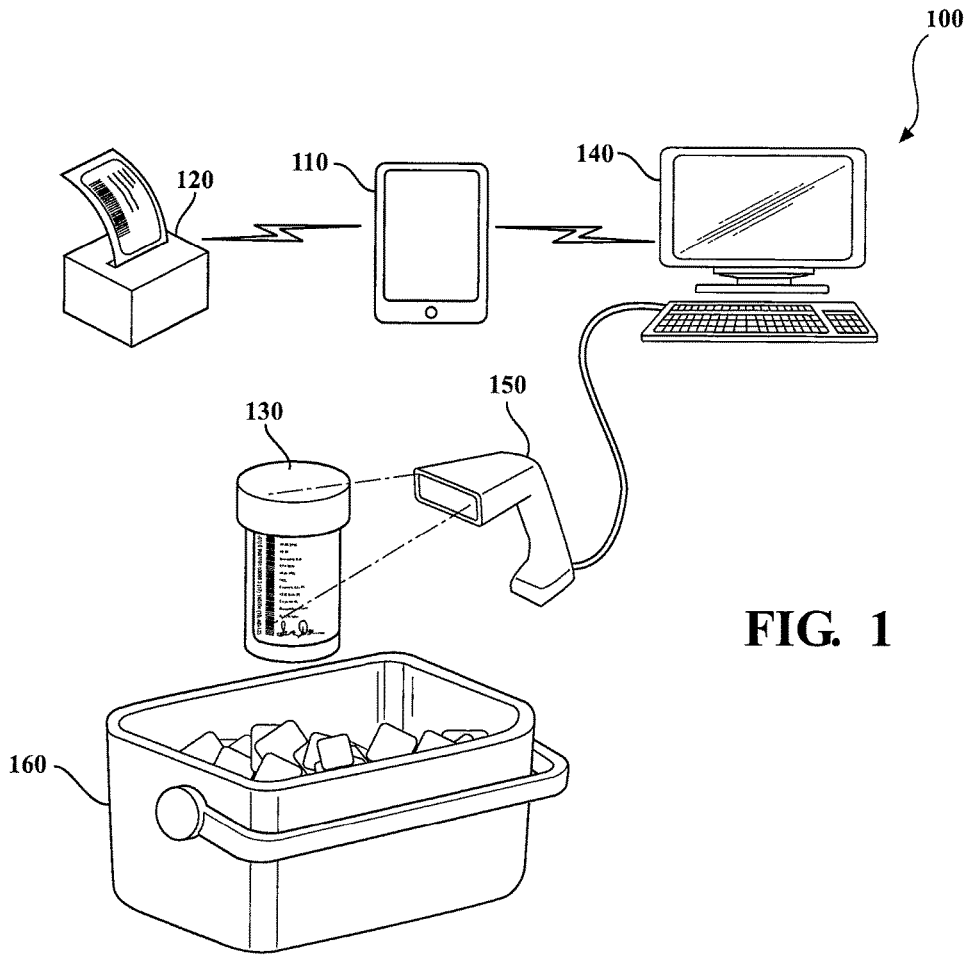
FIG. 1 is a block diagram schematic of an exemplary system for managing sample collection data and documentation from sample collection through sample delivery.

In the following detailed description, numerous specific details are set forth in order to provide a thorough understanding of the examples as defined in the claimed subject matter, and as an example of how to make and use the examples described herein. However, it will be understood by those skilled in the art that claimed subject matter is not intended to be limited to such specific details, and may even be practiced without requiring such specific details. In other instances, well-known methods, procedures, and ingredients have not been described in detail so as not to obscure the invention defined by the claimed subject matter.

Some portions of the detailed description that follow are presented in terms of algorithms and/or symbolic representations of operations on data bits and/or binary digital signals stored within a computing system, such as within a computer and/or computing system memory. An algorithm is generally considered to be a self-consistent sequence of operations and/or similar processing leading to a desired result. The operations and/or processing may take the form of electrical and/or magnetic signals configured to be stored, transferred, combined, compared and/or otherwise manipulated. It has proven convenient at times, principally for reasons of common usage, to refer to these signals as bits, data, values, elements, symbols, characters, terms, numbers, numerals and/or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing", "computing", "calculating", "determining" and/or the like refer to the actions and/or processes of a computing platform, such as a computer or a similar electronic computing device that manipulates and/or transforms data represented as physical electronic and/or magnetic quantities and/or other physical quantities within the computing platform's processors, memories, registers, and/or other information storage, transmission, and/or display devices.

Unless specifically stated otherwise, as apparent from the following discussion, it is appreciated that throughout this specification a computing platform includes, but is not limited to, a device such as a computer or a similar electronic computing device that manipulates and/or transforms data represented by physical, electronic, and/or magnetic quantities and/or other physical quantities within the computing platform's processors, memories, registers, and/or other information storage, transmission, reception and/or display devices. Accordingly, a computing platform refers to a system, a device, and/or a logical construct that includes the ability to process and/or store data in the form of signals. Thus, a computing platform, in this context, may comprise hardware, software, firmware and/or any combination thereof. Where it is described that a user instructs a computing platform to perform a certain action, it is understood that "instructs" may mean to direct or cause to perform a task as a result of a selection or action by a user. A user may, for example, instruct a computing platform embark upon a course of action via an indication of a selection, including, for example, pushing a key, clicking a mouse, maneuvering a pointer, touching a touch pad, touching a touch screen, acting out touch screen gesturing movements, maneuvering an electronic pen device over a screen, verbalizing voice commands, and/or by audible sounds. A user may include an end-user.

Flowcharts, also referred to as flow diagrams by some, are used in some figures herein to illustrate certain aspects of some examples. Logic they illustrate is not intended to be exhaustive of any, all, or even most possibilities. Their purpose is to help facilitate an understanding of this disclosure with regard to the particular matters disclosed herein. To this end, many well-known techniques and design choices are not repeated herein so as not to obscure the teachings of this disclosure.

Throughout this specification, the term "system" may, depending at least in part upon the particular context, be understood to include any method, process, apparatus, and/or other patentable subject matter that implements the subject matter disclosed herein. The subject matter described herein may be implemented in software, in combination with hardware and/or firmware. For example, the subject matter described herein may be implemented in software executed by a hardware processor.

Throughout this specification, the terms "COC" and "chain of custody" refer to a document (in paper or electronic format) that chronologically documents all operations/events pertaining to a sample. The COC may include a list of samples, testing instructions, sample details, and/or project-specific information, including, but not limited to mailing addresses, email addresses, billing/payment information, names, and phone numbers. As such, the COC provides a history of the individuals that handle/possess the samples from the time of collection through the delivery of the samples to their final destination, such as a laboratory.

Throughout this specification, the terms "ECOC" and "electronic chain of custody" refer to COC in an electronic format. The ECOC is a file that can be in a variety of formats, such as Excel, CSV, etc., and can be used for a variety of purposes, such as data upload, data storage, and data/information reporting.

As used herein, the term "environmental sample" refers to a sample collected from the soil/ground, air, water, minerals, and plants, specifically excluding a sample collected from a human or animal.

Referring to FIG. 1, FIG. 1 shows a block diagram schematic of an exemplary system 100 for managing sample collection data and documentation from sample collection through sample delivery. In this example, the system 100 is particularly configured for collecting samples, such as environmental samples, identifying and labeling the samples, tracking the samples, and creating an ECOC file to document a particular sample collection process and to transmit the corresponding data and documentation. The samples may be collected from all kinds of media, such as, but not limited to soil samples, ground water samples, surface water samples, waste water samples, storm water samples, air samples, plant samples, asbestos samples, and lead paint samples. The system 100 may be used for collecting samples in a variety of fields, including, but not limited to environmental, forensic, and medical.

In this example, the system 100 comprises at least one mobile computing device adapted to be operated at a sample collection site ("field mobile computing device") 110, a label printer 120, a first sample collection device 130, at least one computing system 140, and a barcode scanner/reader 150. The field mobile computing device 110 may be any computing device, such as, but not limited to a smartphone, smart watch, tablet, notebook computer, computer server, personal digital assistant, mobile device, handheld device, or any other functionally equivalent device known in the art.

The field mobile computing device 110 comprises a database and a processor connected to the database. The field mobile computing device 110 also comprises a memory, the memory-storing instructions executable by the processor. The memory may include any volatile, non-volatile, magnetic, or electrical media, such as a random access memory (RAM), read-only memory (ROM), flash memory, or any other digital media. In some examples, the field mobile computing device 110 comprises a camera capable of capturing a digital image or video and at least one sensor, such as an image sensor.

The field mobile computing device 110 is capable of transmitting and receiving sample information to and from the label printer 120 and the computing system 140 via a wireless connection. The wireless communication may occur over a network, or other forms of indirect communication. Communications may occur directly over a local area network (LAN), wide area network (WAN) such as the Internet, cloud environment, telecommunications network, WiFi, Bluetooth, or any other communications technique. In other examples, the communication between the field mobile computing device 110 and the label printer 120 or the field mobile computing device 110 and the computing system 140 may occur via a wired connection.

The first sample collection device 130 may be a bottle, container, cooler, drum, brick, or a functionally equivalent device used to collect and transport samples. In some examples, the first sample collection device 130 may be placed into a second sample collection device 160, which is larger than the first sample collection device 130, to more readily store, preserve, and transport the sample located in the first sample collection device 130. The second sample collection device 160 may be a bottle, container, cooler, drum, brick, or a functionally equivalent device that can collect, preserve, and transport a plurality of first sample collection devices 130. In some examples, the second sample collection device 160 also includes ice or cooling packs/gels in order to preserve samples during their transportation from the field to designated facilities.

In some embodiments, the system 100 may also include a mobile software application configured to operate and be stored on the field mobile computing device 110. The mobile software application provides a user interface that accepts input directly from the operator of the field mobile computing device 110 in order to perform various functions of the system 100. In some embodiments, the operator of the field mobile computing device 110 may be referred to as a sample collector, project manager, or field technician. The mobile software application may also receive information from other mobile computing devices or the computing system 140.

In some examples, the mobile software application is pre-configured with specific collection instructions and data, such as, but not limited to, the size of the first sample collection device 130, the type of the first sample collection device 130 (plastic, glass, etc.), the type of preservative, special handling instructions, the number of sample collection devices, and the hold times for each test that the environmental facility uses. In some examples, the mobile software application uses the pre-configured specific collection instructions to determine which tests need to be conducted, and in turn, which sample collection devices need to be filled. In other examples, the mobile software application may be configured to determine the appropriate test requirements and sample collection device requirements on the fly in response to various field observations and/or activities, such as, but not limited a sudden pipeline leak, a tanker rollover, a leaking tank, or other spill/release.

Additionally, the mobile software application may include an application for sorting and processing sample collection information, such as, but not limited to the name of the operator of the field mobile computing device 110, sample site project information, addresses, sample identification information, dates, and times. The mobile software application is configured to communicate the sample collection information to the label printer 120, which is portable and located remotely from the computing system 140. In some examples, the label printer 120 is located at the site of sample collection.

In response to communication received from the field mobile computing device 110, the label printer 120 prints the appropriate number of labels with specific sample collection information and data corresponding to each sample collection device to be filled with a sample. In addition, the label printer 120 prints a unique identifier, such as a barcode, on each label that serves to associate the printed sample collection information and data, and/or the first sample collection device 130, and/or the location/setting of the sample for downstream tracking, processing, and analysis of the sample and/or the sample location. As a result, each printed label may include sample collection data and information, which directly corresponds to a complete ECOC files, and sample location data and information, which are all stored on the field mobile computing device 110. The label printer 120 may be any conventional label printer. One example of the label printer 120 is a 12 V thermal label printer.

The barcode scanner/reader 150 is in communication with the computing system 140 and is capable of transmitting sample collection information and the barcode to the computing system 140. The sample collection information and the barcode are transmitted to the computing system 140 when the barcode scanner/reader 150 scans the barcode on the first sample collection device 130.

In other examples, the label printer 120 may be a thermal printer that prints a QR code on each label that serves to associate the printed sample collection information and data, and/or the first sample collection device 130, and/or the location/setting of the sample for downstream tracking, processing, and analysis of the sample and the sample location. A QR code can be generated embedding certain information about the sample and actions to be performed on the sample. This QR code may then be used later and scanned by the computing system 140 at a facility that accepts the sample labeled with the QR code. In some embodiments, the QR code is scanned/read by a stereoscopic camera in communication with the computing system 140. Once the QR code is scanned, data input fields may be pre-populated with the ECOC and sample information.

In yet other embodiments, the label printer 120 may print an RFID tag/chip on each label that serves to associate the printed sample collection information and data, and/or the first sample collection device 130, and/or the location/setting of the sample for downstream tracking, processing, and analysis of the sample and the sample location.

In some examples, the computing system 140 may be operated by a sample testing facility, such as a laboratory or other entity which administers sample testing for environmental, forensic, and/or medical purposes. In some examples, the computing system 140 is a laboratory computer associated with the receipt of samples and sample associated information and data. In some examples, the computing system 140 comprises a processor, a camera, such as a stereoscopic camera, and memory, the memory-storing instructions executable by the processor. The memory may include any volatile, non-volatile, magnetic, or electrical media, such as a random access memory (RAM), read-only memory (ROM), flash memory, or any other digital media. The computing system 140 may comprise any computing device, whether or not mobile, such as a desktop computer, laptop computer, tablet, phone, or network server. The computing system 140 can receive and transmit sample collection information and data to and from the field mobile computing device 110, computing systems operated by other environmental facilities, regulators, field technicians, and project managers. Communication may occur directly over a local area network (LAN), wide area network (WAN) such as the Internet, cloud environment, telecommunications network, WiFi, Bluetooth, or any other communications technique.

Figure 2:
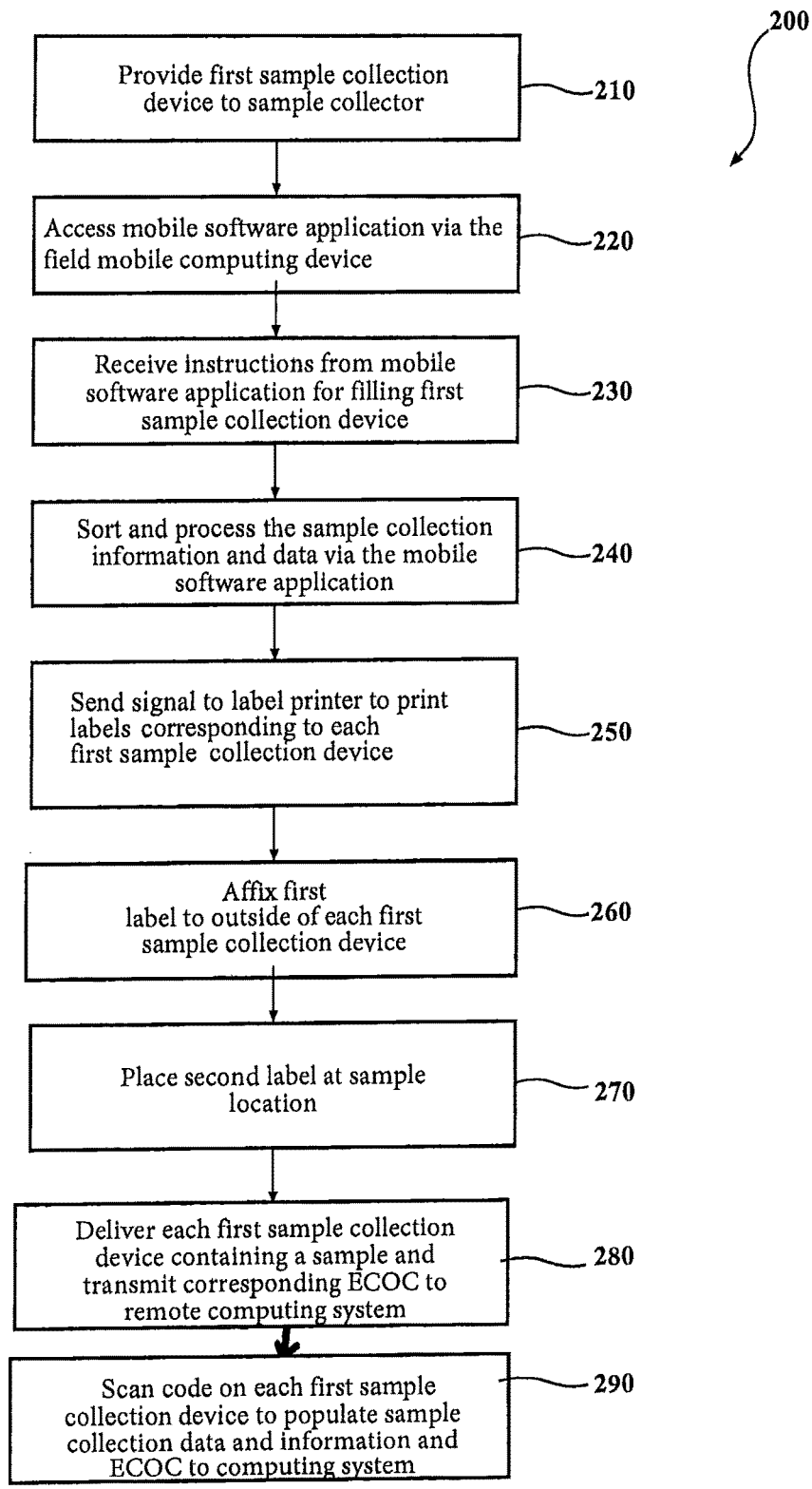
FIG. 2 is a flow chart depicting a process for managing sample collection information and data using the system of FIG. 1.

Referring to FIG. 2, FIG. 2 shows a flow chart of an exemplary method 200 for managing sample collection information and data using the system 100 of FIG. 1. As shown in block 210, the method 200 begins when a sample testing facility, such as a laboratory, provides a first sample collection device 130 to an individual responsible for collecting the sample. This individual may be referred to as a field technician, project manager, sample collector, operator, and the like. In block 220, the individual registers for and logs into the mobile software application on the field mobile computing device 110 by providing the necessary authorization information, such as a username and password.

Next, as shown in block 230, the mobile software application on the field mobile computing device 110 provides instructions for identifying and filling the first sample collection device 130. In some examples, the instructions are based on specific, pre-defined sample collection instructions provided by the sample testing facility. In other examples, the instructions are based on spontaneous decisions of the individual collecting the samples in response to various field observations and/or activities.

In some examples, the specific, pre-defined sample collection instructions and data are immediately downloaded to the field mobile computing device 110 through a synchronization feature on the mobile software application. The sample collection instructions and data include, but are not limited to the types of samples, the size of the first sample collection device 130, the location of the sample, the material of the first sample collection device 130 (plastic, glass, etc.), the type of preservative, special handling instructions, the number of sample collection devices, and the hold times for each test that the predetermined environmental facility uses. Examples of field observations and/or activities that affect the spontaneous decisions include, but are not limited to a sudden pipeline leak, a tanker rollover, a leaking tank, or other spill/release.

In block 240, the mobile software application on the field mobile computing device 110 sorts and processes the sample collection information and data, including, but not limited to the name of the operator of the field mobile computing device 110, sample site project information, addresses, sample identification information, dates, and times. The mobile software application also collects GPS coordinate information from the field mobile computing device 110 at the time of sampling collection and at the time of any custody transfer. As a result, the custody transfer indicates who is doing the transfer, the samples that are being transferred, the time that the transfer occurred, and the location of the transfer by capturing the GPS coordinates.

Figure 5:
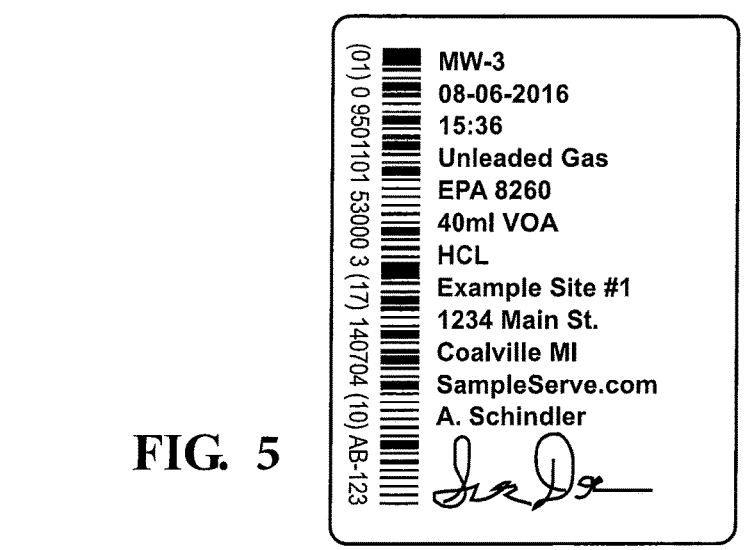
FIG. 5 is a schematic plan view of an exemplary label with a barcode generated by the system of FIG. 1.

Then, in block 250, the mobile software application sends a signal to the label printer 120 directing it to print the appropriate number of labels at the sample collection site with the specific sample collection information and data corresponding to each first sample collection device 130 to be filled and corresponding to the location of the collected sample. Each printed label also includes a code/identifier that may associate the sample collection information and data with an ECOC file. The sample collection information and data is stored on the field mobile computing device 110. In some examples, the code/identifier is specifically associated with a record number found in the ECOC file. FIG. 5 shows a plan view of an exemplary label printed by the label printer 120 at the sample collection site with a barcode generated by the system 100 of FIG. 1.

In block 260, a first label is affixed to the outside of the first sample collection device 130 is labeled in the field. In some examples, upon completion of sample collection for a defined period of time, the field technician transmits the ECOC files corresponding to the first sample collection device 130 to the computing system 140 operated by the sample testing facility prior to delivery of the samples. The ECOC files may be electronically transmitted to the computing system 140 by any conventional means, such as via email.

In block 270, a second label is placed at the site of sample collection. In non-limiting examples, the site may be a physical structure, such as a building, a drum, a brick, a tree, a branch, etc. In other non-limiting examples, the site may be a location on or in the ground. Like with the first label, the unique identifier or code on the second label may be a bar code, a QR code, or RFID tag. The second label may associate the collected sample with the site/location of the collected sample. In some embodiments, the second label has the same data and information as the first label. In other embodiments, the second label has different data and information than the first label.

Upon scanning the second label at the location of the collected sample, analytical results and/or sample collection data and/or information may be accessed and displayed on the field mobile computing device 110 via the mobile software application. A non-limiting example of some of the results generated from scanning the second label may be an indication of the presence, type, and/or amount of specific substances/matters found at the sample location. For example, the field mobile computing device 110 may be configured to provide a Pass/Fail indication corresponding to the presence of specific substances/matters at the location of sample collection. Even after the completing tests on the sample(s) and reporting results, the second label at the sample location may be scanned to readily provide data and information regarding the location of the collected sample and associate it with the data and information corresponding to the collected sample, such as test results and collection data.

In block 280, the computing system 140 accesses the ECOC files upon receipt of the first sample collection device 130, which contains the samples. In some examples, the ECOC data and documentation is accessed using a separate "plug-in" application that operates on the computing system 140.

Then, in block 290, the barcode scanner/reader 150 scans the barcode on the first sample collection device 130 and populates the relevant sample information to the computing system 140. In other examples, a stereoscopic camera on the computing system 140 scans the QR code on the first sample collection device 130. In some examples, as the first sample collection device 130 is scanned, the associated ECOC data and documentation is automatically uploaded into the environmental facility's existing database. In some examples, the existing database is known as the Laboratory Information Management System (LIMS). Since the ECOC files are the complete sample collection information required by the laboratory, no additional sample collection information needs to be entered manually.

Figure 3:
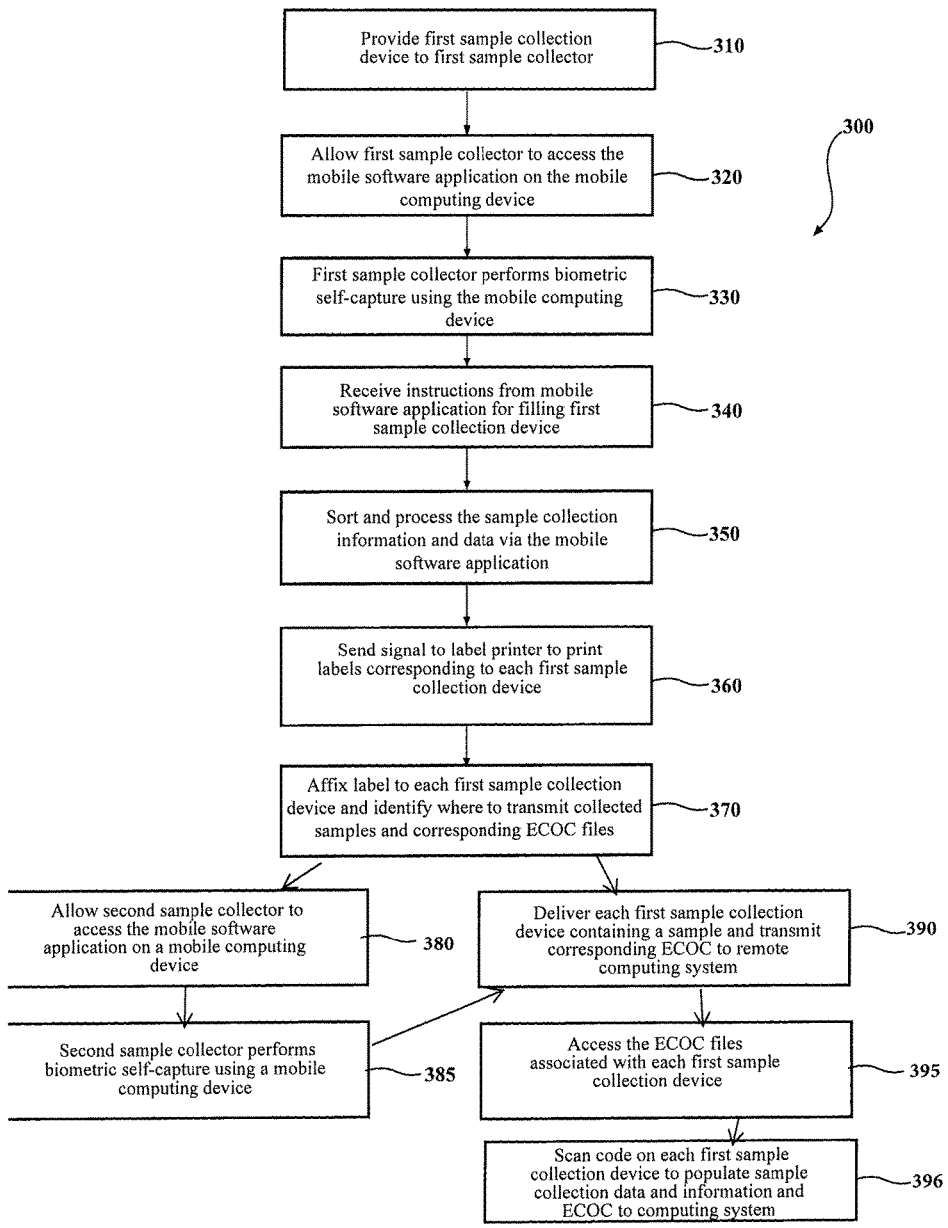
FIG. 3 is a flow chart depicting a second process for managing sample collection information and data using the system of FIG. 1.

Referring to FIG. 3, FIG. 3 shows a flow chart of another exemplary method 300 for managing sample collection information and data using the system 100 of FIG. 1. As shown in block 310, the method 300 begins when a sample testing facility, such as a laboratory, provides a first sample collection device 130 to a first individual responsible for collecting the sample. In block 320, the first individual registers for and logs into the mobile software application on the field mobile computing device 110 by providing the necessary authorization information, such as a username and password.

Figure 6:
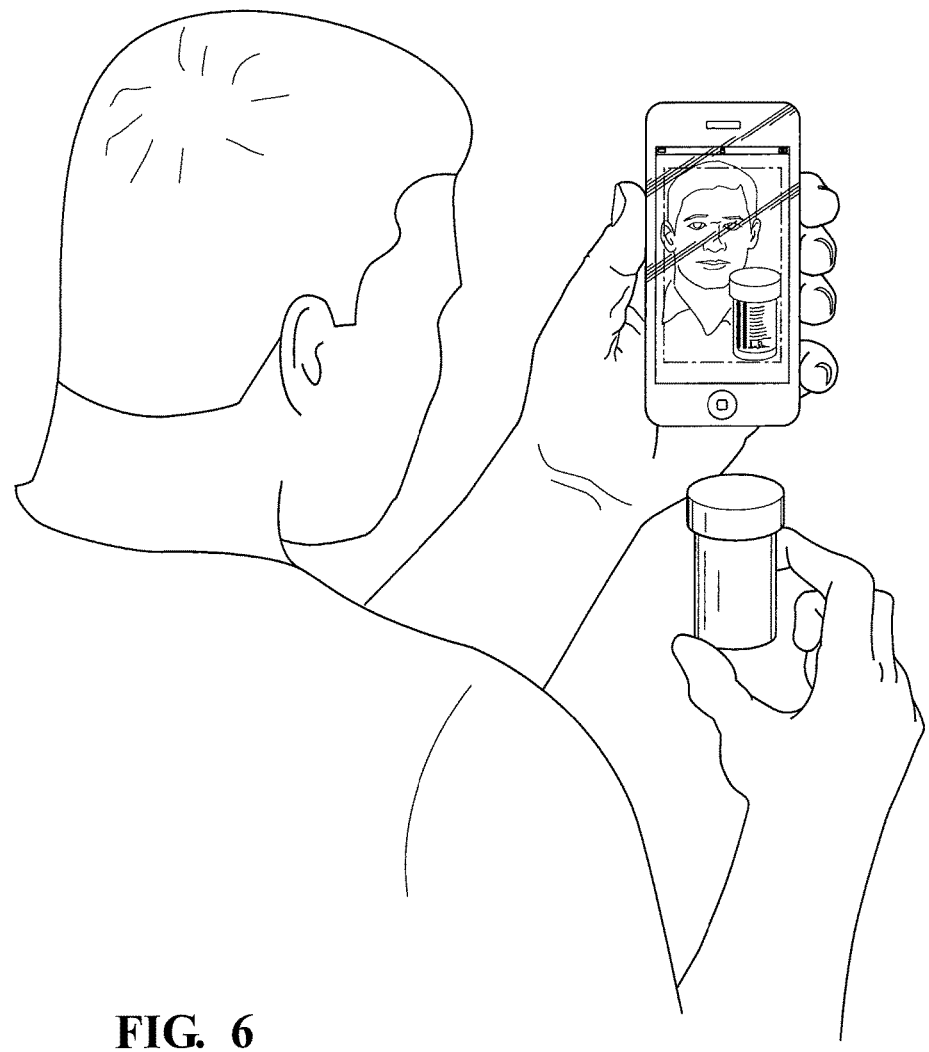
FIG. 6 is a schematic depiction of the field mobile computing device of FIG. 1 capturing a close-up image of an individual.
Figure 7:
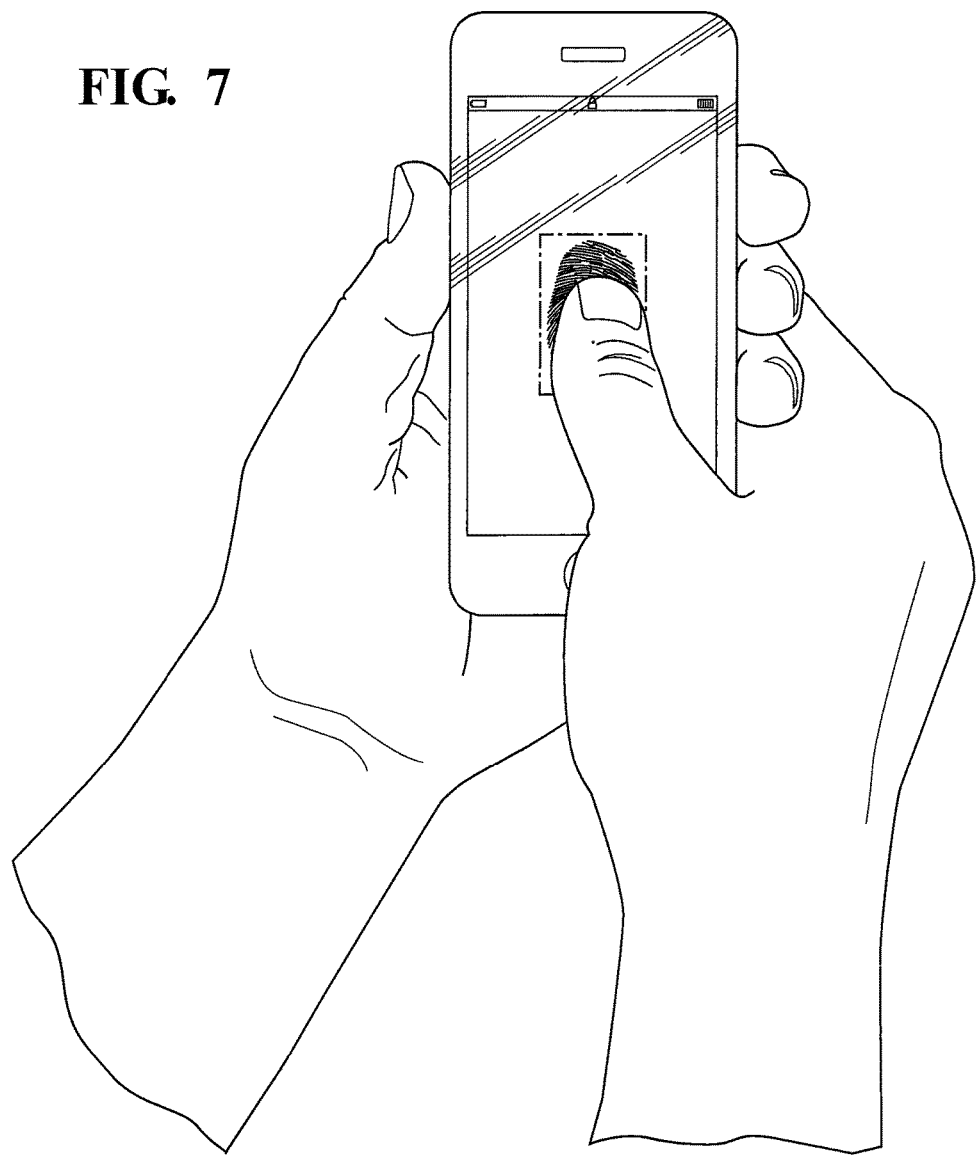
FIG. 7 is a schematic depiction of the field mobile computing device of FIG. 1 capturing a fingerprint impression of the individual.

Next, as shown in block 330, the first individual performs a biometric self-capture using the field mobile computing device 110 in order to more accurately and securely track the individual(s) that have handled and/or transported samples. The biometric self-capture may also allow for authentication of the specific individual(s) that has handled samples when compared to the COC. In one example, the individual takes a close-up image or video of himself/herself ("selfie") using the camera on the field mobile computing device 110, as shown in FIG. 6. In another example, the individual provides his/her electronic signature (e.g., a fingertip signature) in the field mobile computing device 110. In yet another example, the individual provides a fingerprint impression that may be acquired by a finger-print reader located on the field mobile computing device 110, as shown in FIG. 7.

In some examples, the field mobile computing device 110 may capture more than one type of biometric information, such as facial recognition information, retinal recognition information, movement detection information, voice recognition information, and light reflection information, from the same first individual. Each sample testing facility determines its own desired levels of authentication and security for the handling and transport of its samples. As a result, each sample testing facility determines the types and amount of biometric information to be collected from the individual(s) responsible for handling and/or transporting the samples.

As shown in block 340, the mobile software application on the field mobile computing device 110 provides instructions for identifying and filling the first sample collection device 130. In some examples, the instructions are based on specific, pre-defined sample collection instructions provided by the sample testing facility. In other examples, the instructions are based on spontaneous decisions of the first individual collecting the samples in response to various field observations and/or activities.

In block 350, the mobile software application on the field mobile computing device 110 sorts and processes the sample collection information and data, including, but not limited to the name of the operator of the field mobile computing device 110, sample site project information, addresses, sample identification information, dates, and times.

Then, in block 360, the mobile software application sends a signal to the label printer 120 directing it to print the appropriate number of labels at the sample collection site with the specific sample collection information and data corresponding to each first sample collection device 130 to be filled and corresponding to the location of the collected sample. Each printed label also includes a code/identifier that may associate the sample collection information and data with an ECOC file. The sample collection information and data is stored on the field mobile computing device 110. In some examples, the code/identifier is specifically associated with a record number found in the ECOC file.

In block 370, a first label is affixed to the outside of the first sample collection device 130 and a second label is placed at the site of sample collection. The site may be a physical structure, such as a building, a drum, a brick, a location in/on the ground, etc. Like with the first label, the unique identifier or code on the second label may be a bar code, a QR code, or RFID tag. The second label may associate the collected sample with the site/location of the collected sample. In some embodiments, the second label has the same data and information as the first label. In other embodiments, the second label has different data and information than the first label.

Upon completion of sample collection for a defined period of time, the first individual determines whether the collected sample(s) and corresponding ECOC file should be transmitted to a second individual responsible for additional sample collection and/or sample handling or transmitted directly to the sample testing facility. In some examples, a different individual may be responsible for transporting the samples to the sample testing facility from the individual that actually collected the samples in the field. In some examples, the mobile software application is configured to provide the first individual with instructions for determining whether to transmit the sample(s) and ECOC to a second individual or directly to the sample testing facility. If the collected sample(s) and the ECOC files are not transmitted to a second individual, they are transmitted directly to the computing system 140 operated by the sample testing facility prior to delivery of the samples, as shown in block 390.

If the collected sample(s) and the ECOC files are transmitted to a second individual via the second individual's field mobile computing device, the second individual registers for and logs into the same mobile software application in the same manner as the first individual, as shown in block 380. The second individual then performs a biometric self-capture in the same way as the first individual, as shown in block 385. The biometric information from the second individual may either be captured on the field mobile computing device 110 that is passed from the first individual to the second individual or through the second individual's own field mobile computing device.

Once the second individual finishes collecting samples in the field, the second individual determines whether the collected sample(s) and corresponding ECOC file should be transmitted to a third individual responsible for additional sample collection and/or sample handling or transmitted directly to the sample testing facility. In some examples, the mobile software application is configured to provide the second individual with instructions for determining whether to transmit the sample(s) and ECOC to a third individual or directly to the sample testing facility.

In block 395, the computing system 140 accesses the ECOC data and documentation upon receipt of the first sample collection device 130, which contains the samples. In some examples, the ECOC data and documentation is accessed using a separate "plug-in" application that operates on the computing system 140.

Then, in block 396, the barcode scanner/reader 150 scans the code on the first sample collection device 130 and populates the relevant sample information to the computing system 140. In other examples, a stereoscopic camera on the computing system 140 scans the QR code on the first sample collection device 130. In some examples, as the first sample collection device 130 is scanned, the associated ECOC data and documentation is automatically uploaded into the environmental facility's existing database. In some examples, the existing database is known as the Laboratory Information Management System (LIMS). Since the ECOC files are the complete sample collection information required by the laboratory, no additional sample collection information needs to be entered manually.

Figure 4:
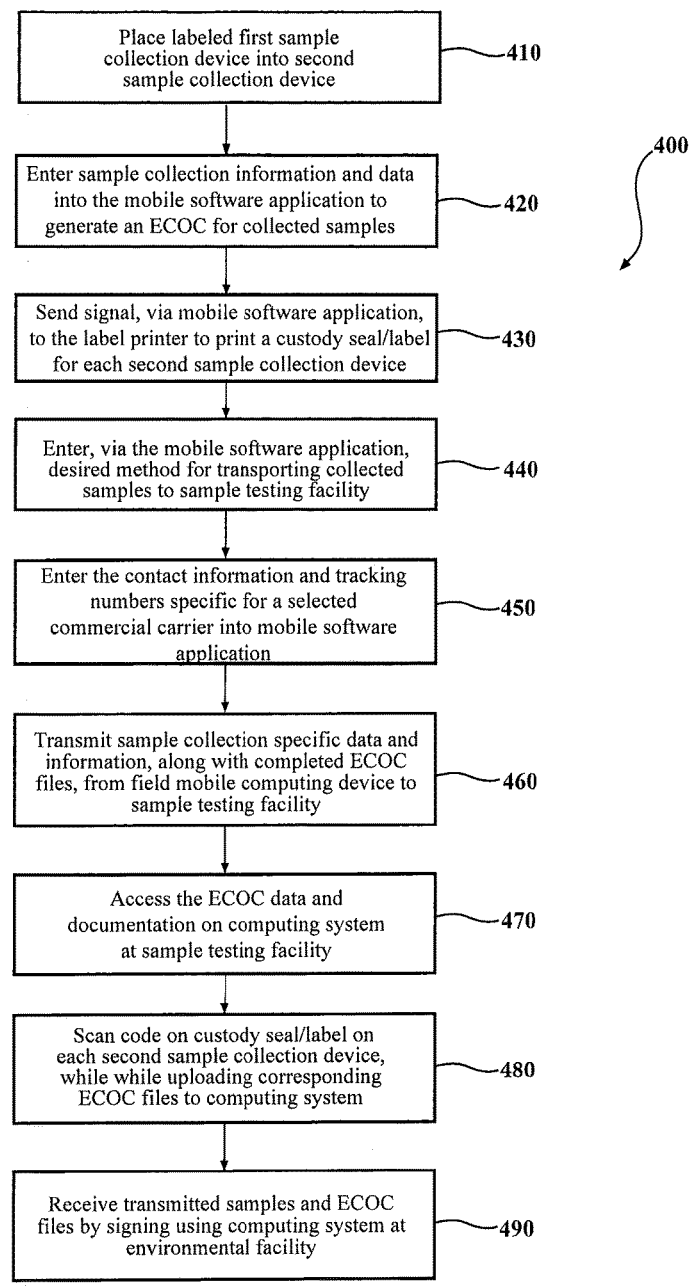
FIG. 4 is a flow chart depicting a process for managing sample collection information and data using a plurality of sample collection devices.

Referring to FIG. 4, FIG. 4 shows a flow chart of an exemplary method 400 for managing sample collection information and data using a plurality of sample collection devices. In this exemplary method 400, the labeled first sample collection device 130 is placed into the second sample collection device 160 for better preservation and storage of the sample(s), as shown in block 410. In order to better preserve and store the samples contained in a plurality of first sample collection devices 130 until the samples are ready to be transported to a sample testing facility, the first sample collection devices 130 are placed into the second sample collection device 160.

In block 420, the individual handling the samples triggers the mobile software application to generate an ECOC for the collected samples commencing from the time that the previous ECOC was generated for these samples. In initiating the generation of the ECOC, the mobile software application prompts the individual to provide specific sample collection information, such as the amount of first sample collection devices 130 and second sample collection devices 160 needed to transport the collected samples to the desired sample collection facility; the contact information for the sample collection facility that will be receiving the collected samples; and the number of samples to be transported. If more than one sample collection facility is used, the mobile software application generates a separate ECOC for each sample collection facility.

For any sample that is transported from the collection site to the sample testing facility by courier or is transported by more than individual within a company/organization, each individual involved in the transport of the sample and/or the second collection device 160 is required to register an account and create a user profile with the mobile software application.

Upon confirmation of the number of second sample collection devices 160, the mobile software application sends a signal to the label printer 120 directing it to print one custody seal/label specific for each of the second sample collection devices 160, according to block 430. Each custody seal/label includes a barcode or a QR code and information and/or data specific for the collected sample, such as contact information for the individual collecting the sample; the date and time the custody seal/label was generated; project-specific details and parameters; information regarding the intended environmental facility; and the amount of first sample collection devices 130 and second sample collection devices 160 (e.g. cooler 1 of 5, cooler 2 of 5, etc.) needed to transport the collected samples to the intended sample testing facility. Each barcode or QR code is specifically associated with a unique record number in the ECOC, corresponding to a specific sample and its sample collection information and data. The sample collection information and data is stored on the field mobile computing device 110.

According to block 440, the mobile software application prompts the field technician to identify the method for transporting the collected samples to the intended sample testing facility. Exemplary methods include commercial carrier (such as FedEx, UPS, etc.), courier (such as lab courier), or direct (in-person) delivery. Since signatures on the COC are not obtained from the commercial carrier when transporting the samples, the custody seal/label is particularly important for determining sample custody issues.

If a commercial carrier is selected for transporting the samples, custody seals/labels are specifically applied to each of the second collection devices 160 to be transported and contact information of the specific commercial carrier is entered into the mobile application software, in block 450. In addition, tracking numbers specific for the commercial carrier may be entered into the mobile application software through the user interface and become part of the ECOC file until the samples are transported to the desired environmental facility. In some examples, the custody seals/labels are applied over the seam between the lid and body of the second collection device 160, such as a cooler. As a result, the custody seal/label is broken when the cooler is opened.

Prior to delivering the samples to the designated commercial carrier, the name of the commercial carrier is entered into the mobile application software as the "Transferee" on the COC, along with the estimated time that the samples were delivered to the commercial carrier. Since this process parallels existing techniques for completing a COC on paper, this process can be readily implemented by sample collectors and sample testing facilities.

In block 460, all of the data and information pertaining to the collection of a specific sample is electronically transmitted, along with the completed ECOC, to the sample testing facility's predetermined computing system 140. The completed ECOC may be displayed in electronic data file form and PDF form and may look identical to a COC completed on paper, with the signatures in the same locations. The computing system 140 accesses the ECOC data and documentation upon receipt of the samples in the second sample collection device 160. In some examples, the ECOC data and documentation is accessed using a separate "plug-in" application that operates on the computing system 140, according to block 470.

Then, in block 480, the barcode or the QR code on the custody seal/label located on each of the second sample collection devices 160 can be scanned by the mobile software application or by the barcode scanner/reader 150 or the stereoscopic camera in communication with the computing system 140. Once each second sample collection device 160 is scanned and confirmed as received, the associated ECOC data and documentation for each individual sample is automatically accessed and uploaded into the sample testing facility's existing database. This allows for the individual receiving the samples to scan and enter the first sample collection devices 130 into the existing database for processing and/or analysis. In some examples, the existing database is known as the Laboratory Information Management System (LIMS). Since the ECOC files are the complete sample collection information required by the laboratory, no additional sample collection information needs to be entered manually.

In block 490, the individual confirms receipt of the samples and the ECOC at the sample testing facility. In some examples, the individual receiving the samples may sign his/her name using a touchscreen on the computing system 140. In other examples, the individual receiving the samples may complete a biometric self-capture, such as providing facial recognition information, retinal recognition information, movement detection information, voice recognition information, and/or light reflection information. The biometric information is then captured by the computing system 140 and/or LIMS.

The system 100 allows a first registered user (referred to herein as a "transferor") to readily transfer the ECOC and samples to a second registered user (referred to herein as a "transferee") through the field mobile computing device 110 of the transferor in order to indicate that the ECOC and samples are being transferred. In some examples, after logging in to the mobile software application, the transferor provides his/her biometric information to the field mobile computing device 110. The transferee then logs into the same mobile software application either using the field mobile computing device 110 received from the transferor or using his/her own field mobile computing device. The transferee's biometric information is then captured using a field mobile computing device. Upon accessing the mobile software application, the transferee can view the ECOC, along with the number of second sample collection devices 160 and samples transferred by the transferor.

In examples where the transferee is using a field mobile computing device distinct from that used by the transferor, the transferor enters the contact information for the transferee on the mobile software application of the field mobile computing device 110 and transfers the samples to the transferee. The transferee then scans the barcodes or QR codes located on the custody seal/label of the second sample collection devices 160 using features of the transferee's mobile computing device, such as the mobile computing device's camera. Upon logging into the system 100 and entering his/her signature on the mobile computing device using his/her fingertip, the transferee would be able to view the transferred COC (in electronic or printed form), along with the scanned sample information and data associated with the transferred COC through his/her mobile computing device.

The successful transfer of the COC/ECOC is deemed completed once the transferee can view the COC/ECOC. The communication of information and data, such as the COC/EOC, from the field mobile computing device 110 to the transferee's mobile computing device may occur directly over a local area network (LAN), wide area network (WAN) such as the Internet, cloud environment, telecommunications network, WiFi, Bluetooth, or any other communications technique. The COC/ECOC files will be transmitted in the same way as they are transmitted when the transferor and transferee both use the field mobile computing device 110. There are no limits regarding the amount of transferees that may receive the samples prior to their transport to the sample testing facility.

When the second sample collection devices 160 are transported directly to a sample testing facility by the sample collector, custody seals/labels are not required to be applied to the second sample collection devices 160. However, in some examples, the custody seals/labels are still applied to the second sample collection devices 160. In these examples, the barcode or the QR code on the custody seal/label located on each of the second sample collection devices 160 can be scanned by the mobile software application or by the barcode scanner/reader 150 in communication with the computing system 140. Then, the individual receiving the samples in the sample testing facility signs his/her name using either a touchscreen on the computing system 140 or a camera on the field mobile computing device 110, which is in direct communication with the computing system 140 and/or LIMS.

Referring to FIGS. 8*a* and 8*b*, FIGS. 8*a* and 8*b* each show plan views of exemplary user interfaces for Low Flow Sampling Display of sample collection information and data generated using the system of FIG. 1. The Low Flow Sampling Display user interfaces in FIGS. 8*a* and 8*b* allow for the input of various sample collection information and data, such as, but not limited to the following:
  1. Sample location/Well identification number;
  2. Operator name;
  3. Sample collection times;
  4. Sample pH;
  5. Sample flow rate;
  6. Sample temperature;
  7. Sample conductivity;
  8. Sample turbidity;
  9. Sample reduction potential;
  10. Sample dissolved oxygen; and
  11. Site name.

The Low Flow Sampling Display in FIGS. 8*a* and 8*b* allow for the manipulation of the sample collection information and data through the creation of tables, graphs, maps, and images. In addition, the mobile software application allows for the following actions to be performed by the user through the Low Flow Sampling Display user interface:
  1. Stop data collection and start collecting sample and print labels;
  2. Capture GPS;
  3. Generate picture;
  4. Re-print individual sample bottle labels;
  5. E-mail data;
  6. Upload data to website; and
  7. Synchronize to store, upload, and email data.

Referring to FIG. 9, FIG. 9 shows a plan view of an exemplary user interface for Grab Sampling of sample collection information and data generated using the system of FIG. 1. The Grab Sampling user interface in FIG. 9 allows for the input of various sample collection information and data, such as, but not limited to the following:
  1. Site name;
  2. Sample location/Well identification number;
  3. Operator name;
  4. Comments;

5. Sample collection times;
6. Sample pH;
7. Sample flow rate;
8. Sample temperature;
9. Sample conductivity;
10. Sample turbidity;
11. Sample reduction potential; and
12. Sample dissolved oxygen.

The Grab Sampling user interface in FIG. 9 allows for the manipulation of the sample collection information and data through the creation of tables, graphs, maps, and images. In addition, the mobile software application allows for the following actions to be performed by the user through the Grab Sampling user interface:

1. Capture GPS;
2. Generate picture;
3. Print individual sample bottle labels;
4. E-mail data;
5. Upload data to website; and
6. Synchronize to store, upload, and email data.

Other features of the mobile software application allow for the synchronization of the mobile software application with the field mobile computing device 110 and/or the computing system 140. This feature allows for the immediate transmission of all sample collection information and data relating to a particular project work scope. As a result, sample collection information and data may be quickly and easily transmitted to and from the mobile software application.

As used herein, computing system and computer readable storage media do not cover signals or other such unpatentable subject matter. Only non-transitory computer readable storage media is intended within the scope and spirit of claimed subject matter.

It will, of course, be understood that, although particular examples have just been described, the claimed subject matter is not limited in scope to a particular example or limitation. Likewise, an example may be implemented in any combination of compositions of matter, apparatuses, methods or products made by a process, for example.

In the preceding description, various aspects of claimed subject matter have been described. For purposes of explanation, specific numbers, percentages, components, ingredients and/or configurations were set forth to provide a thorough understanding of claimed subject matter. However, it should be apparent to one skilled in the art having the benefit of this disclosure that claimed subject matter may be practiced without the specific details. In other instances, features that would be understood by one of ordinary skill were omitted or simplified so as not to obscure claimed subject matter. While certain features and examples have been illustrated or described herein, many modifications, substitutions, changes or equivalents will now occur to those skilled in the art. It is, therefore, to be understood that the appended claims are intended to cover all such modifications or changes as fall within the true spirit of claimed subject matter.

What is claimed is:

1. A method for managing collection data and/or information corresponding to at least one environmental sample using a mobile software application configured to operate on a mobile computing device, the method comprising:
    (i) providing at least one sample collection device;
    (ii) accessing the mobile software application on the mobile computing device;
    (iii) receiving a set of pre-configured instructions from the mobile software application for processing and analyzing field data at a site, wherein the field data comprises a plurality of parameters;
    (iv) processing and analyzing the field data at the site;
    (v) transmitting a signal to the mobile computing device based on the values of the plurality of parameters in the processed and analyzed field data, wherein the signal comprises instructions for when to collect the environmental sample, where to collect the environmental sample within the site, and the type of the environmental sample to collect;
    (vi) collecting the environmental sample at the site;
    (vii) printing a first label at the site corresponding to the sample collection device and a second label at the site corresponding to a location of sample collection, wherein the first label includes a first unique identifier and the second label includes a second unique identifier, wherein the first unique identifier and the second unique identifier are both associated with the environmental sample;
    (viii) affixing the first label to the sample collection device and placing the second label at the site;
    (ix) transmitting an electronic chain of custody corresponding to the environmental sample to a computing system located remote from the site prior to delivering the sample collection device to the computing system; and
    (x) scanning the first unique identifier on the sample collection device to populate the collection data and/or information corresponding to the environmental sample and the electronic chain of custody in the computing system.

2. The method of claim 1, wherein the site is a physical structure.

3. The method of claim 1, wherein the site is on the ground or in the ground.

4. The method of claim 1, wherein each of the first unique identifier and the second unique identifier are barcodes and/or QR codes, wherein the barcodes and/or QR codes are associated with a unique number in the electronic chain of custody.

5. The method of claim 1, further comprising scanning the second unique identifier at the site.

* * * * *